United States Patent [19]

Steiger

[11] 4,186,743
[45] Feb. 5, 1980

[54] PERFUMING SELF-ADHERING NAPKINS

[75] Inventor: Fred H. Steiger, East Brunswick, N.J.

[73] Assignee: Personal Products Company, Milltown, N.J.

[21] Appl. No.: 882,299

[22] Filed: Feb. 28, 1978

[51] Int. Cl.² ............... A61F 13/16; A61F 13/18; A61F 13/20
[52] U.S. Cl. ............... 128/284; 128/290 R; 128/290 W
[58] Field of Search ......... 128/268, 284, 287, 290 R, 128/290 W, 156; 222/1; 428/343; 401/132-133; 24/DIG. 11, 205.16 D; 206/0.7, 85; 229/84

[56] References Cited

U.S. PATENT DOCUMENTS

| | | | |
|---|---|---|---|
| 2,615,754 | 10/1952 | Lindenberg | 206/0.7 |
| 2,986,477 | 5/1961 | Eichel | 428/343 |
| 2,988,461 | 6/1961 | Eichel | 428/343 |
| 3,490,454 | 1/1970 | Goldfarb et al. | 128/285 |
| 3,585,998 | 6/1971 | Hayford et al. | 128/284 |
| 3,598,123 | 8/1971 | Zaffaroni | 128/268 |
| 3,640,629 | 2/1970 | Geiser | 401/132 |
| 3,685,734 | 8/1972 | Paciorek et al. | 424/21 |
| 3,691,271 | 9/1972 | Charle et al. | 128/290 R |
| 3,913,580 | 10/1975 | Ginocchio | 128/284 |
| 3,981,304 | 9/1976 | Szpur | 401/133 |

FOREIGN PATENT DOCUMENTS 962805  2/1975  Canada .................................. 128/296

*Primary Examiner*—Robert W. Michell
*Assistant Examiner*—Thomas Wallen
*Attorney, Agent, or Firm*—Jason Lipow

[57] ABSTRACT

A sanitary napkin is provided having a pressure-sensitive adhesive element on the surface thereof for adhering to the crotch portion of the undergarment. The adhesive element is further provided with a protective releasable layer having adhered thereto microcapsules containing a deodorant material. Upon peeling the protective releasable layer from the adhesive element, the deodorant material is released in a controlled manner.

5 Claims, 4 Drawing Figures

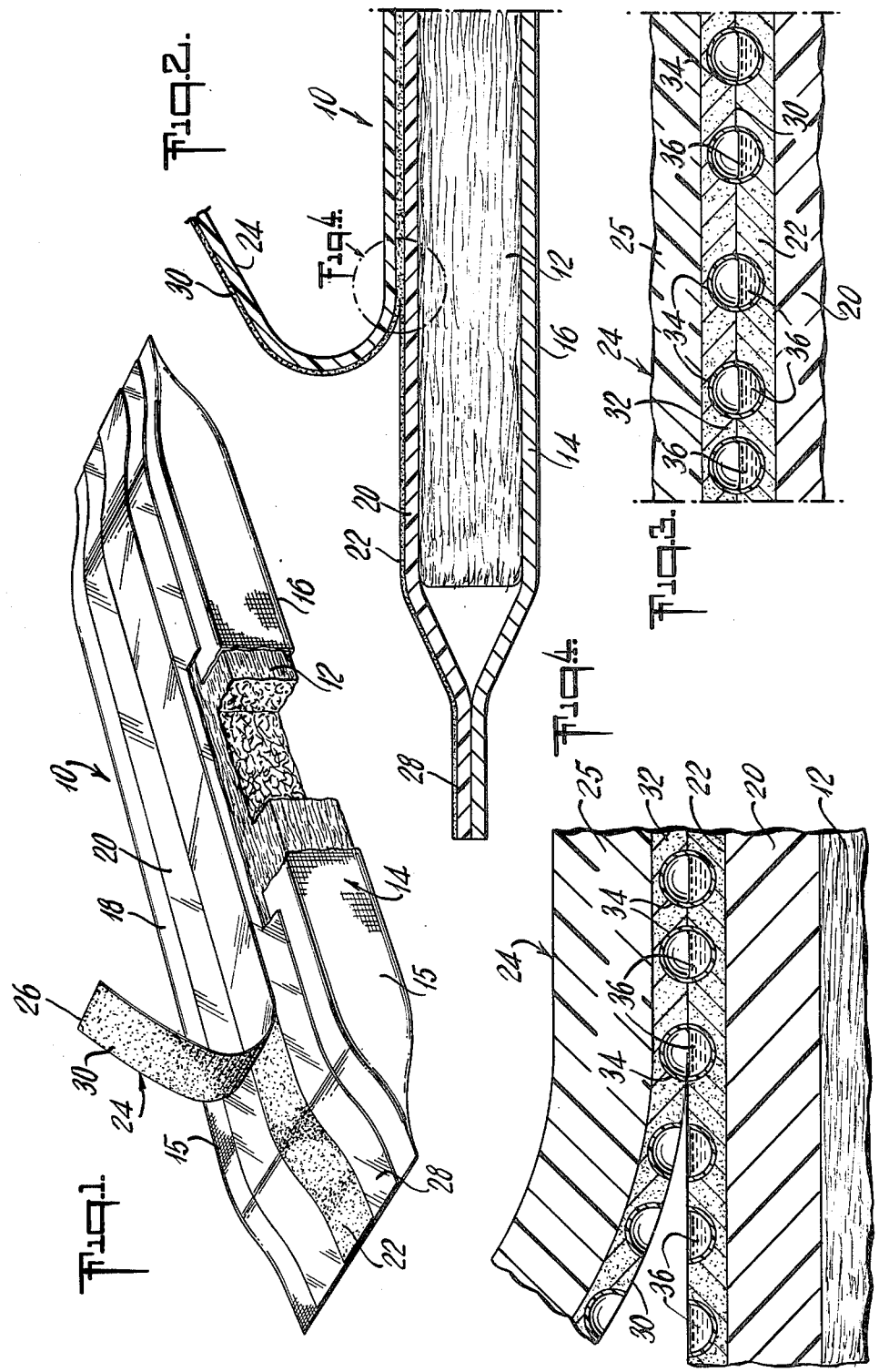

PERFUMING SELF-ADHERING NAPKINS

BACKGROUND OF THE INVENTION

This invention relates to sanitary napkins and more particularly relates to sanitary napkins having adhesive attachment means and being provided with perfumes or deodorants for masking or otherwise reducing the perception of malodorous body fluids absorbed and retained by the napkins in use.

Sanitary napkins generally comprise an elongated absorbent body or pad of such absorbent materials as wood pulp, cotton, wadding or the like having two major surfaces, one of which is to be worn against the body of the user and the other away from the body, i.e., toward the user's undergarment. The surface worn against the body is often provided with a porous cover for containing the absorbent material and this cover may extend completely or partially around the pad. The surface worn away from the body may be covered with an impervious cover or barrier film to preclude body fluids absorbed by the pad from transferring through the pad and onto the undergarment or other clothing of the wearer. This barrier film can be provided on the outer most surface of the napkin or below the porous cover if such porous cover extends around the entire pad. Recently, the above-described sanitary napkins have been provided with a layer of pressure-sensitive adhesive overlying a portion of the outer-most surface of the napkin on the surface worn away from the body, i.e., the garment contacting surface. The purpose of this pressure-sensitive adhesive is to adhere to the crotch portion of the user's undergarment and to preclude the napkin from shifting from the intended in-use position.

The above-described napkins are generally worn during menstruation for a period of time up to several hours in the course of which time they absorb and retain a substantial quantity of menstrual fluid. This retained menstrual fluid is known to contain various highly malodorous compounds such as amines or fatty acids. To obviate the potential for embarrassment and discomfort for the user, the art has long sought methods for masking or otherwise deodorizing such products. These prior art suggestions have considered adding, generally to the absorbent pad, deodorizing agents or perfumes in the form of either powders or liquids. Several drawbacks are associated with these prior art efforts. From a manufacturing point of view, powders are difficult to incorporate into sanitary napkins in that they tend to dust out or settle after the napkin has been handled during manufacturing, packaging and distribution. Liquid perfume compositions, on the other hand, tend to diffuse throughout the product and affect the stability of elements of the napkin such as the barrier film or the pressure-sensitive adhesive.

Perhaps most important, is a problem inherent in the application of masking scents, either in powder or liquid carriers, to a product such as a sanitary napkin. In order to be effective, a scent must volatilize and ultimately reach the olfactory sensors of humans. Thus the incorporation of a scent into a napkin by whatever means employed heretofore, meant that the scent began to volatilize from the point of manufacturing, through packaging and storing and finally during use. To insure that sufficient scent is available during use, manufacturers have had to incorporate large excess quantities of scent into their products and have had to tolerate the release of this scent in such undesired places as in their plants, warehouses and in retail stores. This has proven to be economically wasteful and aesthetically undesirable. Moreover in use the scent may be trapped within the absorbent material of the napkin between the body of the user and the barrier film and therefore the intensity of the fragrance as perceived by the wearer as well as by others is diminished relative to what it would be if the same quantity of fragrance material were employed in some part of the napkin that was more accessible to available air currents. Thus the location of the fragrance material in the absorbent pad necessitates the use of greater quantities of fragrance materials which increase the cost of the product.

One suggestion for solving this problem is found in U.S. Pat. No. 3,490,454 issued to A. Goldford and W. Geiler on Jan. 20, 1970. Taught therein is a sanitary napkin in which, or on which, is placed at least one layer of a multiplicity of rupturable capsules which may contain among other materials, deodorants. It is contemplated in the above-described reference that the act of applying the napkin will serve to rupture certain of the capsules, releasing the deodorants for the first time and at the time of use. Unfortunately, the degree of handling of the product by the user varies widely from user to user and from time to time. Concomitant therewith, the numbers of capsules ruptured will vary greatly and hence the quantity of deodorant released. To insure that a sufficient quantity of deodorant is released, the manufacturer must uneconomically provide a great excess number of deodorant filled capsules.

Accordingly, the art has heretofore failed to find a satisfactory method for perfuming or deodorizing sanitary napkins.

SUMMARY OF THE INVENTION

In accordance with this instant invention, a sanitary napkin is provided with means for releasing a perfume or other deodorant only at the time of use and not prior thereto, and in an amount which is predictable and hence controlled from user to user and from time to time. The invention contemplates employing such means in a sanitary napkin comprising an elongated absorbent body having a body contacting side, i.e., the side to be worn against the body, and a garment contacting side, i.e., the side to be worn against the user's undergarment. Provided on the garment contacting side of the napkin is a pressure-sensitive element for adhering to the user's undergarment and maintaining the napkin in place when worn. Adhered to and overlying said pressure-sensitive adhesive element is a protective strip which is placed over the adhesive element to protect the same from dirt and unintended adhesion prior to use but which can be easily peeled off and discarded at the time of use.

In accordance with the teachings of this invention, the protective strip is provided, on the surface which contacts the pressure-sensitive adhesive element, with a plurality of discrete rupturable capsules containing a deodorant material, e.g., a perfume composition. The rupturable capsules are choosen so that upon peeling the protective strip from the adhesive element when the napkin is to be used, a substantial portion of the capsules rupture, releasing a controlled quantity of deodorant material.

BRIEF DESCRIPTION OF THE DRAWINGS

The improvements of the present invention will be more readily understood by reference to the following drawings in which:

FIG. 1 illustrates a sanitary napkin incorporating the teachings of this invention and illustrating in perspective view with parts removed and with the protective strip partially peeled away;

FIG. 2 is a partial longitudinal, cross-sectional view of the napkin of FIG. 1;

FIG. 3 is an enlarged schematic longitudinal cross-sectional view of a portion of the protective strip used in the napkin of this invention; and FIG. 4 is an enlarged schematic view of the portion of the napkin illustrated in FIG. 2 which includes the interface between the peeled back protective strip and the adhesive element.

DETAILED DESCRIPTION OF THE INVENTION

Referring now to FIGS. 1-4, there is illustrated a sanitary napkin 10 embodying the teachings of this invention. The napkin 10 comprises an absorbent body or pad 12 which can be made from any of the many well-known materials having body fluid absorbing properties such as comminuted wood pulp, cotton linters, rayon fibers, cotton staple, bleached sulfite creped wadding, regenerated cellulose foams, natural sponges, chemically modified cellulosics, synthetic absorbent materials such as hydrophilic polyurethane and the like, and combinations of these materials. When the absorbent material is in the form of loosely associated particulate matter, e.g., fibers, powders, crumbs or the like, the absorbent body 12 is provided with a body fluid pervious cover 14 which covers the body contacting surface 16, i.e., the surface intended to be worn against the body of the user. Cover 14 may also cover the sides 15 of the absorbent body as well as portions of the garment contacting surface 16, i.e., the surface intended to be worn against the body of the user and against the crotch portions of an undergarment. The pervious cover 14 shown in the embodiment of the drawings may be a knitted, woven, or non-woven fabric or paper made from a variety of cellulosic or synthetic materials. It will also be understood that in certain circumstances, as when the absorbent body 12 has sufficient integrity, the need for a pervious cover may be obviated. In such circumstance there may be no cover. For example, the absorbent body may take the form of molded polyurethane or cellulosic foam or of fibrous absorbent material having an adhesive binder dispersed therein to give the body 12 structural integrity. In these instances, a pervious cover may be unnecessary.

Overlying the surface 18 worn away from the body is a fluid impervious barrier sheet 20 which can be made, for example, of such film-forming materials as polyethylene, polypropylene, cellophane, or from impregnated fluid repellent paper or similar fluid impervious sheet-like materials.

The barrier sheet 20 and the cover 14 may be sealed together to envelop the absorbent body by means well known in the art such as, for example, by use of adhesives (not shown).

The outer surface of barrier sheet 20 is provided with a layer of pressure sensitive adhesive, preferably taking the form of at least one narrow element 22 which preferably extends in a band throughout the longitudinal direction of the napkin. As described above, the adhesive is provided to adhere the napkin to the crotch portion of the wearer's undergarment and retain the napkin in proper position during use. The adhesive element may comprise any of a large number of pressure sensitive adhesives available on the market, including for example, the so-called cold pressure-sensitive adhesives such as the acrylate adhesives, e.g., vinyl acetate/2 ethylhexyl acrylate copolymer which is generally combined with tackifiers such as, for example, ethylene amine. Alternatively, the adhesive may comprise the rapid setting thermoplastic (hot melt) adhesives such as block copolymers exemplified by styrene-isoprene, styrene-ethylene-butylene and butadiene-styrene copolymers. The adhesive band may also comprise a two-sided adhesive tape.

The adhesive element is protected by a releasable protective strip 24 overlying the adhesive band 22 to protect the adhesive from dirt and unintended adhesion prior to use. Immediately prior to use, this protective layer is peeled off, FIGS. 1, 2 and 4 illustrating the layer 24 in a partially peeled position. it has been noted that almost invariably the user will peel this protective layer from the adhesive in the same manner, to wit: the user will grip tab 28 of the napkin between two fingers of one hand and the end 26 od the protective strip 24 between two fingers of the other hand and pull these apart. This invention takes advantage of this fact to provide means for insuring that a controlled amount of a deodorant material is made available only just prior to use.

Specifically, in accordance with this invention, the surface 30 of the protective strip 24, which surface is to contact the adhesive element 22, is provided with a multiplicity of small frangible capsules containing deodorant materials. This is illustrated schematically in FIG. 3 which represents an enlarged cross-sectional view of a portion of the protective strip 24. The strip 24 is generally comprised of a paper board material 25 of thin gauge, e.g., 3–6 mils, so as to be sufficiently flexible to be easily peeled from the adhesive element. Affixed to this paper board is a layer comprising a multiplicity of discrete, small frangible capsules 34, hereinafter microcapsules, containing a deodorant composition, e.g., a perfume composition. Several methods may be used to adhere the microcapsules to the board. For example, a slurry of microcapsules dispersed in an adhesive may be made up and the surface 30 of the protective strip may be coated with this slurry. A wide variety of adhesives will be suitable for this purpose, such as for example, polyethylenes, polyesters, polysiloxanes, acrylics, or block copolymers of styrene. FIG. 3 illustrates such a coating 32 containing dispersed therethrough microcapsules 34 containing deodorant material 36.

FIG. 4 illustrates schematically one mechanism believed to be the operative one in insuring that a controlled amount of deodorant material 36 is released from the microcapsules just prior to use. This figure illustrates schematically a greatly enlarged area of the napkin shown in FIG. 2 taken at the interface between the peeled and unpeeled portions of the protective strip 24. Referring to the unpeeled portion of the strip 24 on the right hand side, as FIG. 4 is viewed, it can be seen that a portion of at least some of the microcapsules 34 are embedded and gripped by the adhesive element 22 when the strip 24 is applied in its protective position prior to use. Referring now to the peeled portion of the strip on the left hand side of FIG. 4, it can be seen that the act of peeling causes these microcapsules to rupture releasing the deodorant material 36. Because the forces applied and the manner in which the strip 24 is peeled from the adhesive element almost invariably is constant from user to user and from time to time, those factors which control the number of capsules ruptured and hence the quantity of deodorant material released are entirely within the control of the manufacturer. Such factors are, the rupture strength of the capsules, the number and distribution of the capsules, the quantity of deodorant in each capsule and the relative adhesive of the capsules to the board and to the adhesive element as compared to the rupture strength of the capsules. With respect to the latter factor, it is clear that both the force required to pull the capsule from the adhesive or from the board must be greater than the force required to rupture the capsule. If this condition is met, capsules embedded within the adhesive will rupture.

It will be appreciated that the enlarged illustrations in the drawings are highly idealized and that in practice not all capsules will be at the surface 30 of the protective strip but, instead, may be entirely covered by the coating 32. In this case, such capsules will not be available to be gripped by the adhesive element 22 and hence will not rupture in accordance with the mechanism described above. Many of such coated capsules will rupture, however, by the crushing action exerted on them when bending back the strip 24 in the act of peeling it from the adhesive. Again, to whatever extent capsules are ruptured in this manner, the number ruptured will be consistent from use to use and will only vary with the physical configuration of the napkin which is in the control of the manufacturer.

Microcapsules for use in this invention can be made by many of several well-known encapsulating processes. Examples of appropriate processes include chemical encapsulating processes and mechanical encapsulating processes. A mechanical encapsulating process is characterized, generally, by including impingement of droplets of the material to be encapsulated (i.e., in the case of this invention, a perfume or other deodorant composition) upon liquid or semi-solid films of intended capsule wall material; separation of the thereby encapsulated droplet from the film of impingement; and solidification of the capsule wall material. Chemical encapsulating processes generally include combining a first reactive material in a continuous phase capsule manufacturing vehicle and a second reactive material into droplets to be encapsulated. The droplets are then dispersed in the manufacturing vehicle and interfacial polymerization between the reactive materials is effected. Liquid-liquid phase separation of the polymeric capsule wall material from the vehicle is carried out wherein the phase-separated polymeric material wets and enwraps the dispersed droplets to be encapsulated.

Capsule wall materials suitable for use in accordance with the teachings of this invention include any appropriate polymeric film-forming material. For example, capsules may be made from natural hydrophilic polymeric materials such as gelatin, gum arabic, starch, carrageenin, and zein; natural polymeric materials modified in some way such as ethyl cellulose, carboxymethyl cellulose, shellac, resin and nitrocellulose; and other polymeric materials such as polyvinylalcohol, polyethylene, polystyrene, polyacrylamide, polyether, polyester, polybutadiene, silicone, epoxy and polyurethane.

The particular perfume or deodorant encapsulated forms no part of this invention and may be varied to so great a degree as to defy classification or description. Reference is made, instead, to "Cosmetics, Science and Technology," second edition, edited by M. S. Balsam and Edward Sagarin and published by John Wiley & Sons, Inc., of New York, 1972. In particular, reference is made to Chapter 32, "Fragrance" written by M. S. Balsam for examples of the variety of perfume formulations possible.

What is claimed is:

1. In a sanitary napkin comprising an elongated absorbent body having a body contacting surface and a garment contacting surface and provided with a pressure-sensitive adhesive element on said garment contacting surface for adhering said napkin to the crotch portion of an undergarment, means for both protecting said pressure-sensitive adhesive element and for releasing a controlled quantity of a deodorant, said means comprising a protective releasable layer overlying and adhered to said adhesive element and having affixed to the surface thereof in contact with said adhesive element, a controlled quantity of deodorant in pressure-frangible microcapsules whereby, upon removing said protective releasable layer, a controlled portion said microcapsules fracture releasing a controlled quantity of deodorant.

2. The sanitary napkin of claim 1 wherein the protective releasable layer comprises a flexible paper board strip having said microcapsules adhered thereto.

3. The sanitary napkin of claim 2 wherein the paper board strip is about 3 to about 6 mils thick.

4. The sanitary napkin of claim 2 wherein said microcapsules are adhered to the paper board strip in admixture with an adhesive coating.

5. The sanitary napkin of claim 4 wherein at least a portion of said microcapsules extended from the surface of the adhesive coating and are embedded in the pressure sensitive adhesive element.

* * * * *